US 6,618,614 B1

(12) United States Patent
Chance (10) Patent No.: US 6,618,614 B1
(45) Date of Patent: *Sep. 9, 2003

(54) OPTICAL EXAMINATION DEVICE, SYSTEM AND METHOD

(75) Inventor: Britton Chance, Marathon, FL (US)

(73) Assignee: Non-Invasive Technology, Inc., Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,835

(22) Filed: Sep. 8, 1998

Related U.S. Application Data (63) Continuation of application No. PCT/US96/11630, filed on Jul. 12, 1996, which is a continuation-in-part of application No. PCT/US96/00235, filed on Jan. 2, 1996, which is a continuation-in-part of application No. 08/367,939, filed on Jan. 3, 1995, now Pat. No. 5,596,987, application No. 09/077,835, which is a continuation-in-part of application No. PCT/US95/15666, filed on Dec. 4, 1995.

(51) Int. Cl.[7] .................................................. A61B 6/00
(52) U.S. Cl. ........................................ 600/473; 600/476
(58) Field of Search ................................ 600/310, 473, 600/476, 322; 356/39–41; 606/2, 27, 13, 16; 607/88, 91, 93

(56) References Cited

U.S. PATENT DOCUMENTS

| 2,688,971 A | * | 9/1954 | Daniels et al. | |
| 3,068,742 A | | 12/1962 | Hicks, Jr. et al. | 88/14 |
| 3,229,685 A | | 1/1966 | Ringkamp et al. | 128/2.05 |
| 3,412,729 A | | 11/1968 | Smith, Jr. | 128/2.05 |
| 3,461,856 A | | 8/1969 | Polanyi | 128/2 |
| 3,638,640 A | | 2/1972 | Shaw | 128/2 R |
| 3,709,612 A | | 1/1973 | Clemens | 356/178 |
| 3,866,599 A | | 2/1975 | Johnson | 128/2 L |
| 3,994,585 A | | 11/1976 | Frey | 356/40 |
| 3,998,550 A | | 12/1976 | Konishi et al. | 356/39 |
| 4,086,915 A | | 5/1978 | Kofsky et al. | 128/2 L |
| 4,119,406 A | | 10/1978 | Clemens | 422/81 |
| 4,138,727 A | | 2/1979 | Mantz | 364/525 |

(List continued on next page.)

FOREIGN PATENT DOCUMENTS

| DE | 227 044 A1 | 9/1985 |
| DE | 44 10 888 A1 | 10/1995 |
| EP | 0 233 108 A1 | 8/1987 |

(List continued on next page.)

OTHER PUBLICATIONS

Chance et al., "Photon Migration in Muscle and Brain," Photon Migration in Tissues, Plenum Press, pp. 121–135, 1989, Chance, B., ed.

(List continued on next page.)

Primary Examiner—Shawna J Shaw
(74) Attorney, Agent, or Firm—Fish & Richardson P.C.

(57) ABSTRACT

As part of an examination device, an input or output optical coupler device for transmitting photons between an optical source or detector and an examined body part includes an array of optical fibers with end portions freely protruding as cantilevers from a support. The optical fibers have the end portions fabricated, sized and distributed to penetrate freely extending hair when the support is placed on the head or other surface of a subject to make optical contact directly over an array of points with the surface of the scalp or skin below the free hair.

49 Claims, 8 Drawing Sheets

U.S. PATENT DOCUMENTS

| | | | |
|---|---|---|---|
| 4,162,405 A | 7/1979 | Chance et al. | 250/461 |
| 4,167,331 A | 9/1979 | Nielsen | 356/39 |
| 4,223,680 A | 9/1980 | Jöbsis | 128/633 |
| 4,281,645 A | 8/1981 | Jöbsis | 128/633 |
| 4,321,930 A | 3/1982 | Jöbsis et al. | 128/633 |
| 4,380,240 A | 4/1983 | Jöbsis et al. | 128/633 |
| 4,416,285 A | 11/1983 | Shaw et al. | 128/634 |
| 4,510,938 A | 4/1985 | Jöbsis et al. | 128/633 |
| 4,612,938 A | 9/1986 | Dietrich et al. | 128/665 |
| 4,800,885 A | 1/1989 | Johnson | 128/633 |
| 4,805,623 A | 2/1989 | Jöbsis | 128/633 |
| 4,824,242 A | 4/1989 | Frick et al. | 356/41 |
| 4,846,183 A | 7/1989 | Martin | 128/633 |
| 4,908,762 A | 3/1990 | Suzuki et al. | 364/413.09 |
| 4,972,331 A | 11/1990 | Chance | 364/550 |
| 4,978,186 A * | 12/1990 | Mori | |
| 5,088,493 A | 2/1992 | Giannini et al. | |
| 5,090,415 A | 2/1992 | Yamashita et al. | 128/665 |
| 5,106,387 A | 4/1992 | Kittrell et al. | 606/15 |
| 5,119,815 A | 6/1992 | Chance | 128/633 |
| 5,187,672 A | 2/1993 | Chance et al. | 364/550 |
| 5,190,039 A | 3/1993 | Takeuchi et al. | 128/633 |
| 5,300,097 A | 4/1994 | Lerner et al. | 607/93 |
| 5,358,503 A | 10/1994 | Bertwell et al. | 606/27 |
| 5,408,093 A | 4/1995 | Ito et al. | |
| 5,420,607 A | 5/1995 | Miller et al. | |
| 5,551,422 A | 9/1996 | Simonsen et al. | 128/633 |
| 5,596,987 A | 1/1997 | Chance | |
| 5,625,458 A | 4/1997 | Alfano et al. | |
| 5,655,530 A | 8/1997 | Messerschmidt | |
| 5,706,821 A | 1/1998 | Matcher et al. | |
| 5,987,351 A * | 11/1999 | Chance | |
| 6,496,718 B1 * | 12/2002 | Lonky | 600/476 |

FOREIGN PATENT DOCUMENTS

| | | |
|---|---|---|
| EP | 0 280 986 A1 | 9/1988 |
| EP | 0 290 279 | 11/1988 |
| EP | 0 467 459 A2 | 1/1992 |
| WO | WO 92/20273 | 11/1992 |
| WO | WO 94/16615 | 8/1994 |
| WO | WO 96/20638 | 7/1996 |

OTHER PUBLICATIONS

Cui et al., "Experimental Study of Migration Depth for the Photons Measured at Sample Surface," *SPIE*, 1431:180–191, 1991.

Greenfeld, "A Tissue Model For Investigation Photon Migration in Trans–Cranial Infrared Imaging," *Photon Migration in Tissues,* Plenum Press, B. Chance, ed., pp. 147–168, 1989.

Sevick et al., "Analysis of absorption, scattering, and hemoglobin saturation using phase modulation spectroscopy," *SPIE,* 1431:264–275, 1991.

Sevick et al., "Photon migration in a model of the head measured using time –and frequency– domain techniques: potentials of spectroscopy and imaging," *SPIE,* 1431:84–96, 1991.

Weng et al., "Measurement of Biological Tissue Metabolism Using Phase Modulation Spectroscopy Technology," *SPIE,* 1431:161–171, 1991.

* cited by examiner

OPTICAL EXAMINATION DEVICE, SYSTEM AND METHOD

CROSS REFERENCE TO RELATED APPLICATIONS this application is a continuation of PCT application PCT/US96/11630, which is a continuation-in-part of PCT/US96/00235 filed Jan. 2, 1996, which is a continuation-in-part U.S. Ser. No. 08/367,939, filed Jan. 3, 1995 now U.S. Pat. No. 5,596,987 issued Jan. 28, 1997. This application is also a continuation-in-part of PCT/US95/15666, filed Dec. 4, 1995. All of the foregoing are incorporated herein by reference.

BACKGROUND OF THE INVENTION

Continuous wave (CW) spectrophotometers, time resolved (TRS/Pulse), phase -modulation (PMS) and phased array spectrophotometers are all known to have application to medicine. These systems depend upon the ability to couple light into tissue from a light source and to couple light from the tissue to a spaced detector. The difference in the flash produced on the photon migration paltorn by abnormality and normal conditions in the body due to different scattering and absorption of the light produce effects that, in principle, enable the use of spectrophotometric examination of the brain is seen as particularly appropriate for the detection of abnormal conditions, in the brain, especially hematoma but also vascular conditions, tumor, and metabolic conditions. Likewise, examination of breast, testicle and muscle is appropriate.

For practical use in medicine, improvement in optical coupling to the subject, is needed to enable these types of spectrophotometric examination to be widely accepted for clinical or home use.

SUMMARY OF THE INVENTION

According to one aspect of the invention, an input or output optical coupler device for transmitting photons between an optical source or detector and the brain, or other part of the body, comprises an array of optical fibers with end portions that freely protrude as cantilevers from a support in the manner of bristles from a hairbrush, the end regions of the fibers sized and distributed to penetrate freely extending hair on the head or other surface of the subject to make optical contact over an array of points with the surface of the skin or scalp, below the free hair.

Preferred embodiments of this aspect of the invention have one or more of the following features.

An examination device is associated with source and detector in which a set of optical fibers of the hairbrush transmits light to the scalp of a subject from the source, and a set of optical fibers of the hairbrush receives light from the scalp at known distance from the source fibers for transmission to the detector.

The fibers have smooth, enlarged tips that comfortably engage the skin or scalp.

The fibers are resiliently flexible laterally to bend and conform the pattern of fiber tips to variations in the shape of the skull, breast or other portion of the body.

The freely extending end portions of the fibers have a length to diameter ratio of between about 5 and 200. In preferred cases the ratio is between 20 and 150, while in other cases between 50 and 125.

The free end portions of the optical fibers have diameter of the order of 0.1 to 3.0 millimeter and have a length between about 0.5 to 3 cm.

The free end portions of the optical fibers have diameter of about 0.2 to 0.5 millimeter and length between about 1 and 2.5 cm.

The coupler device is constructed as a handheld probe, being sized and configured to be moved and placed against the front, sides and top of the head.

The coupler device is constructed as a handheld probe, being sized and configured to be moved and placed against the inside or outside surfaces of the breast.

The coupler device has fibers disposed in a two dimensional array, each fiber or small groupings of the fibers being associated with a discrete detector so that fiber tips simultaneously engage an area of the subject sufficient to provide data to enable processing to provide a back projection image.

One or a set of coupler devices, as part of a helmet or brassier, have sets of fibers arranged to simultaneously, or sequentially engage front, sides and top of the portion of the head or breast being examined.

In another aspect, the coupler is a conformable brush of fine fibers suitable to be applied to breast, testicles, arm or leg.

Other aspects of the invention comprise a hematoma detector or monitor, a tumor detector, a spectrophotometric imager or a metabolic condition monitor employing the brush coupler or other aspects of the devices shown.

BRIEF DESCRIPTION OF THE DRAWINGS

FIG. 5 illustrates use of a "hairbrush" coupler on the sides and frontal regions of the head; while

FIG. 6A is a cutaway view of the helmet of FIG. 6 illustrating the relationship of the "hairbrush" coupler to a subject with a large head of hair; while

FIG. 13A is a perspective view of a band contrast member for use with the end tip of FIG. 13; while

DESCRIPTION OF THE PREFERRED EMBODIMENTS

Figure 1:
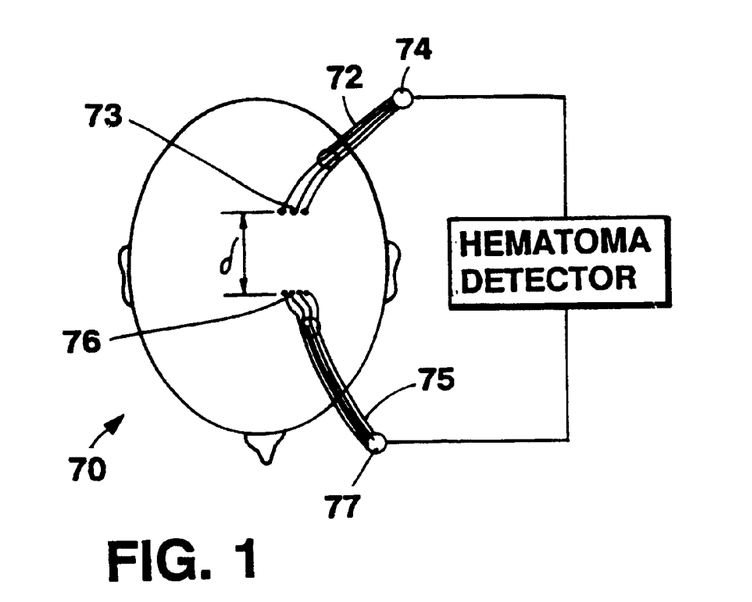
FIGS. 1 and 1A depict a "hairbrush" optical coupling system for optical examination of the brain.

Referring to FIG. 1, an embodiment of a hairbrush optical coupler 70 is shown. This optical coupler is designed to provide optimal coupling of light to and from brain tissue in regions where the skull is covered by hair. Coupler 70 includes at least one source probe 72 and at least one detection probe 75. Source probe 72 is made of approximately twenty optical fibers of 0.5 millimeter to 3 millimeter in diameter and at least one half centimeter in length. Input ports 73 (i.e., irradiation tips) of the fibers of source probe 72 are arranged to form a selected structure (e.g., a matrix, mosaic, circular or linear structure) depending on the desired input geometry and the type of the examined tissue. Each irradiation tip of the fiber may include an optical matching material (e.g., a plastic, a gel-like material, a coating or the like) located between the fiber and the tissue and designed to introduce light efficiently into the examined tissue. At the proximal end, probe 72 has one or more light coupling ports 74. The probe has a single light coupling port made of the fibers bundled together and arranged to achieve efficient coupling of light from a light source (e.g., a light bulb, a light emitting diode, a laser) to the probe. Alternatively, the probe has multiple light coupling ports (e.g., one port per fiber), wherein the generated light is coupled into the fibers sequentially or simultaneously.

Detection probe 75 includes one or more detection ports 76 and one or more light coupling ports 77. Detection probe 75 has a similar design as source probe 72, but may have a larger number of individual fibers in order to collect a sufficient amount of light that has migrated in the tissue. At the proximal end, the detection fibers may also be bundled together to form a single light coupling port 77, which provides good coupling to a wide area detector (e.g., a diode detector, a PMT detector or a MCPD detector). Since source probe 72 and detection probe 75 have a similar construction, they may be used interchangeably. Several source probes and detection probes may be coupled to an optical sequencer or multiplexer constructed to transmit and receive light in a desired manner. The probes are made of cladded fibers to eliminate crosstalk.

Source probe 72 and detection probe 75 are mounted on a support member constructed to achieve a selected position of the fibers and a desired separation of the input ports and the detection ports. The support member can also transmit pressure to the fiber tips for improved coupling of light to the tissue. A connected spectrophotometer (such as a TRS-pulse, PMS, CW, or phased array spectrophotometer) probes deep tissue at large separations of the ports ($\partial$=5 cm to 10 cm) and probes a dermal layer at small separations ($\partial$=0.5 cm to 2 cm).

Figure 1A:
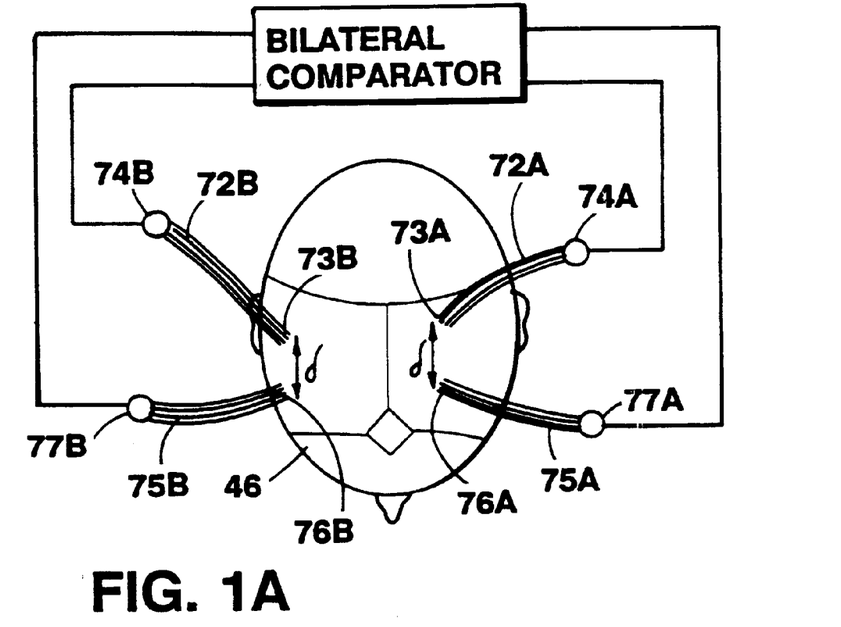

The hairbrush optical coupler can be used for examination of symmetrical tissue regions of the brain, breast, arm, leg or other, as is described in the WO 92/20273 application. The hairbrush optical coupler can be also employed to detect asymmetrical tissue properties of optically symmetrical body regions. FIG. 1A depicts the hairbrush coupler attached to the head; specifically, to the parietal bones of a newborn which still has the characteristic opening called anterior fontanel. Input ports 73A and 73B of source probes 72A and 72B, respectively, are located on symmetrical locations of the corresponding parietal bones (or the temporal bones, the occipital bone, etc.). Detection ports 75A and 75B are spaced the same distance ($\partial$ usually 3 cm to 8 cm) from the corresponding input ports 73A and 73B. The spectrophotometer introduces radiation of a selected wavelength at each input port and detects radiation at each detection port. The spectrophotometer stores the detected data separately and correlates them together or with a stored data corresponding to the individual brain regions to identify any asymmetry in tissue properties. Alternatively, the spectrophotometer measures a differential signal directly. Normal tissue provides a substantially symmetrical signal. A detected asymmetry may be caused by a tissue disease, such as localized bleeding, an asymmetric stroke volume, or another pathological condition. (For example, see S. P. Gopinath et al., J. Neurosurg., 79, 1993.)

In another embodiment, a multifiber hairbrush probe is used for imaging of the brain. For this purpose, a series of semirigid 1 mm fibers is embedded in a styrofoam or plastic helmet. When the helmet is attached to the head, the input ports of the fibers project through the hair to the surface of the scalp. The patient's head is covered by, for example, 4 rows of 8 fibers extending from the frontal region to the occipital region. A larger number of fibers is used when a higher resolution of the image is needed. Each fiber is coupled at its optical coupling port to an optical sequencer or multiplexer. This way any fiber may be coupled to a light source or a light detector of an optical imager described in PCT/US93/05868 or PCT/US95/15694.

Figure 2:
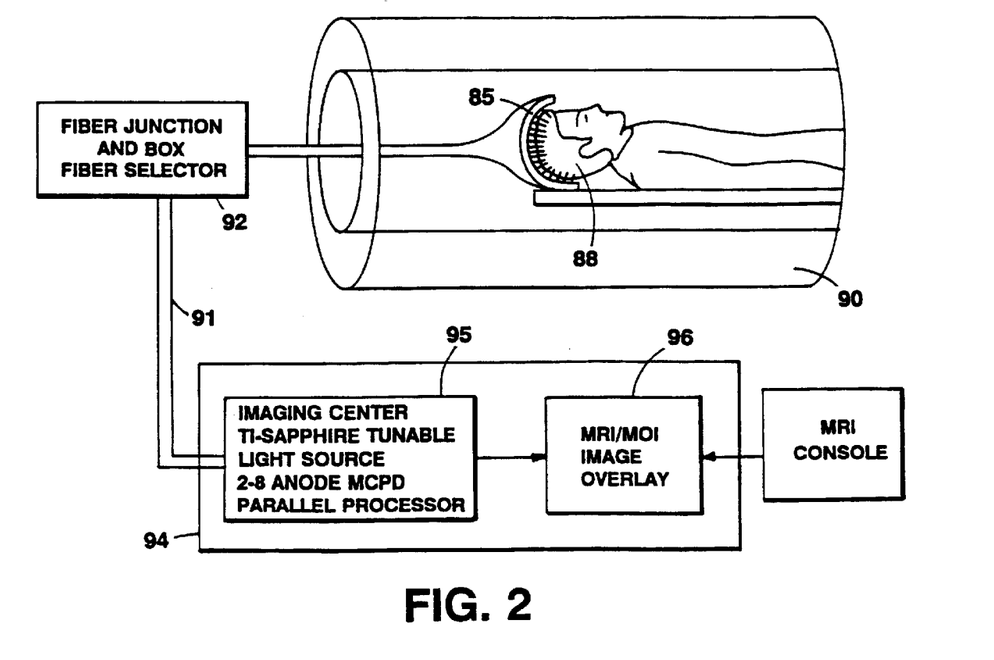
FIGS. 2 and 2A depict a "hairbrush" optical coupling system for optical and MRI examination.

Referring to FIG. 2, in another embodiment, the hairbrush optical coupler is constructed for in vivo examination of tissue using simultaneously magnetic resonance imaging (MRI) and medical optical imaging (MOI) The coupler includes a styrofoam cap 85 with four rows of 8 fibers extending from frontal to occipital region of the patient's head 88 located inside an MRI magnet 90. The optical fibers extend through the hair to the skull and may include ferrite caps. Each fiber is coupled at its optical coupling port to a fiber junction box 92. Fiber junction box 92, located outside of magnet 90, has appropriate electromechanical or electro-optical switches to time sequence the switching of a fiber conduit 91 to any one of the 32 fibers coupled to the head 88. The system employs any one or more fibers for transmission and any other fibers for detection. An MRI/MOI control center 94 includes an imaging center 95 and a computer system 96, which is constructed to create and overlay the optical and magnetic images. Coordination of the optical and MRI images is achieved by MRI/optical markers. Three-dimensional markers are formed by coating the fibers with a film exhibiting a magnetically relaxed water-like signal so that each optical fiber appears on an NMR image. This way an optical image generated by the corresponding source and detector fibers is correlated to the MRI image. Importantly, such "labeled" fibers do not interfere with the NMR examination.

Figure 2A:
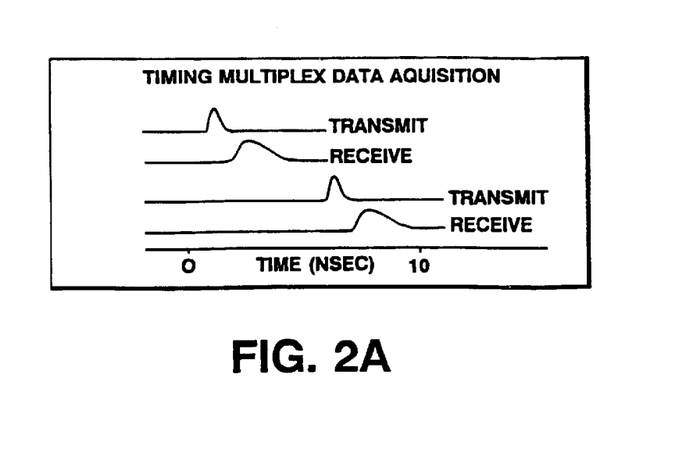

Imaging center 95 employs a TRS system described in U.S. Pat. No. 5,119,815 or in U.S. Pat. No. 5,386,827. The TRS system includes a Ti sapphire tunable laser that generates a series of light pulses of different wavelengths in the NIR region, sensitive to an endogenous or exogenous pigment. The light pulses, generated as shown in a timing diagram of FIG. 2A, are transmitted via fiber conduit 91 to fiber junction box 92. At fiber junction box 92 the signals are multiplexed to the 32 fibers that transmit light to and receive light from appropriate places in the brain. A single optical fiber may also be connected to fiber branches which are attached to various places on the head. The TRS system also includes two 8 multi-anode micro-channel plate detectors. The detector output is sent to a parallel computer that generates images congruent with the MRI scan and completed in approximately the same time as the MRI data.

To achieve proper coupling, the fibers are indexed in space to form an array and are encoded appropriately by an index pad that mimics the tissue positions. This identifies the position of the fibers in the array 1 through 32 relative to a master synchronizing pulse. The imaging sequence consists of a series of pulses transmitted through the main fiber to an identified site at selected intervals (e.g., 5 nanosecond). Each pulse generates a photon migration pattern which is received through an identified optical coupling fiber and is recognized by the central computer as originating from a certain receiving fiber or set of receiving fibers by time encoding. The transmitter pulse stimulates all transmit fibers in sequence. Similarly, the pattern received is a composite of all receiver positions. The imaging console "knows" not only the location of the fiber, but also identifies the signal received from the fiber conduit by its time sequence with respect to the synchronizing pulse. The transmission/reception algorithm consists of a sequence of excitation pulses followed by photon diffusion patterns detected at the particular positions selected specifically for the organ being studied.

The system may use a generic transmission/reception algorithm designed for an average organ or a patient specific algorithm. Furthermore, different algorithms may be used for ipsilateral, contralateral, de novo or recurrent brain bleeding. The optical coupler can be attached to the head (or any part of the body) for longer periods of time to monitor evolution of a tissue state (e.g., brain bleeding, compartment syndrome, or changes in a stroke induced volume) during and after administration of a specific drug. For example, the system can also monitor evolution of a stroke induced volume or changes in intracranial pressure after administration of an osmotic agent (e.g., mannitol, glycerol), texamethasone (with its effects delayed for several hours) or another drug that temporarily reduces brain oedema. The system can also monitor evolution of a solute (e.g., glucose) as it equilibrates in the bloodstream.

Computer system 96 provides an overlay of the two images with contrast due to vascularity/vasculogenesis, blood vessels permeability, proliferation/degeneration of intracellular organelles, or some other tissue characteristics. To properly correlate the optical images to the NMR images, the optical images need to have an adequate contrast. The desired gradient of contrast is accomplished by selecting a suitable contrast agent (i.e., an exogenous pigment) and a wavelength of the introduced light. The spectrophotometer may construct separate images based on the scattering coefficient or the absorption coefficient. Furthermore, imaging center 95 may employ an amplitude modulation system or a CW system rather than the TRS system to increase resolution for some types of images.

In the case of brain examination, for instance, it is desired to detect and localize abnormal regions of 2 to 3 cm in diameter. This is the characteristic size of a hematoma or brain bleed which creates significant risk to the patient. One of the difficulties in employing spectrophotometric examination is the fact that the hair of a subject may be brushed in a certain way which accumulates more hair on one side than on the other. According to the invention, an optical coupler is provided having fibers that have freely protruding end portions of sufficient length to penetrate the hair and enter between the hair follicles. In some instances, especially in the use of large optical fibers, it is practical to use fibers of the order of 32 in number, both for the source and detector, for the purposes of continuous wave (CW) examination.

In other cases, in particular when smaller fibers are employed, a much larger number of fibers is employed, for instance, as many as 1,000 in the case of fibers having a diameter of 0.1 or 0.2 mm.

Single mode fibers, which are characteristically small, are exceedingly effective light carriers for their size, and in some instances are preferred. In those cases especially, enlarged ends are provided on the fibers so that the fiber points do not cause irritation to the head or other examined portion of the patient. In some instances, lenses are also advantageously employed at the ends of the fibers to increase pick up of light whenthe fibers are employed as detecting fibers. In some instances, gradient index fibers which are self-focusing are used for collecting the light, the gradient index fibers extending either entirely to the detector or to a juncture where the light is transferred to a single mode or other transmitting fiber through an effective coupling medium.

According to the invention, it is realized that covering those fibers with protective disposable elements, to be disposable from patient to patient, will ensure a safe imaging condition and efficient use of the equipment.

The embodiments now to be described illustrate these and other features, and diagrammatically illustrate concepts employable for practical manufacture and use of the devices in spectrophotometric monitoring in the medical and home settings.

Figure 3:
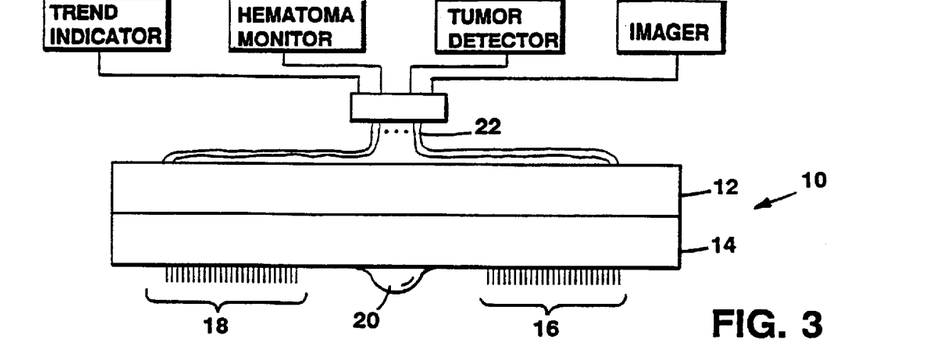
FIG. 3 is a side view and FIG. 3A a bottom plan view of a "hairbrush" optical coupler suitable for monitoring.
Figure 3A:
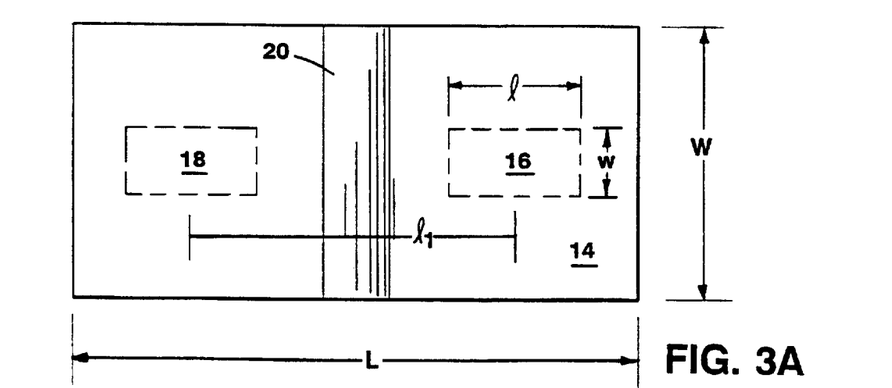

Referring to FIGS. 3 and 3A, a handheld hairbrush optical coupler 10, has two groups of fibers 16 and 18 protruding from the under surface of the lower portion of the hairbrush 14. In one embodiment one group leads to a single light source and the other group leads to a single detector. Between the sections 16, 18 populated by fibers is a barrier 20 of conformable substance adapted to engage the surface and prevent travel of light directly along the surface from source to detector. In the embodiment shown, the groupings of fibers having length 1 of approximately 2 cm and a width w of 1 cm. The overall hairbrush has a length of about 10 cm and a width about 6 cm in the case where $1_1$ is 6 cm.

The design of the embodiment of FIGS. 3 and 3A can be scaled for examination of tissue at different depths keeping in mind that the photon migration path of the scattering light from source to detector follows a banana-like probability configuration in which the mean depth is about one-half the source-to-detector spacing. In an embodiment suitable for hematoma detection where it is wished to examine tissue to a mean depth of approximately 3 cm, the distance 1 between the centers of the source and detector groupings of fibers is approximately 6 cm. For shallower imaging, the distance 1, is shortened. In certain embodiments, the fiber groupings 16 and 18 are made laterally adjustable along the length of the hairbrush handle, whereas in other instances different sizes of hairbrushes are employed for different $1_1$ spacings.

As is described in the literature and in the patent applications that have been incorporated by reference, a continuous wave spectrophotometer such as this, operating in the continuous wave manner, are useful as in a hematoma monitor, and as a tumor detector and as trend indicators with respect to metabolic conditions such as the relationship between hemoglobin and oxyhemoglobin, with respect to blood sugar, and with respect to sodium and potassium metabolism.

There are conditions also in which a form of localization or imaging is achievable with CW depending upon the specific arrangement and nature of the processor employed with the continuous wave scheme.

The hairbrush shown in FIGS. 3 and 3A also has capability in other modes of spectrophotometric examination.

In all cases with respect to brain imaging, the invention proceeds from the realization that while brushed hair introduces irregularities hair follicles at the scalp are relatively evenly distributed symmetrically relative to the forward to back centerplane of the head. By having free-ended optical fiber portions small enough and of sufficient density to penetrate to the scalp and distribute and collect the needed light for spectrophotometric examination, the unbalancing factor of mode of hairbrushing or amount of hair present is eliminated and the spectrophotometric results are regularized. The melanin in the hair follicles still has influence upon the amount of light transferred but comparison of left to right or reference readings reduces the effect of that variable and produces a more useful examination.

The device of FIG. 3 and 3A is therefore useful in particular for lateral comparative reading as will be described further on.

Figure 4:
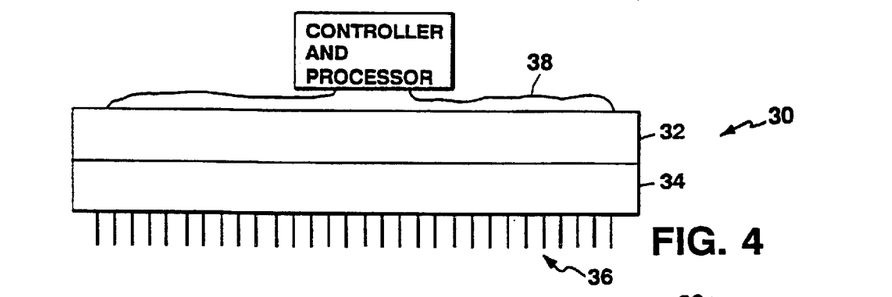
FIG. 4 is a side view and FIG. 4A bottom plan view of a "hairbrush" optical coupler suitable for optical imaging.
Figure 4A:
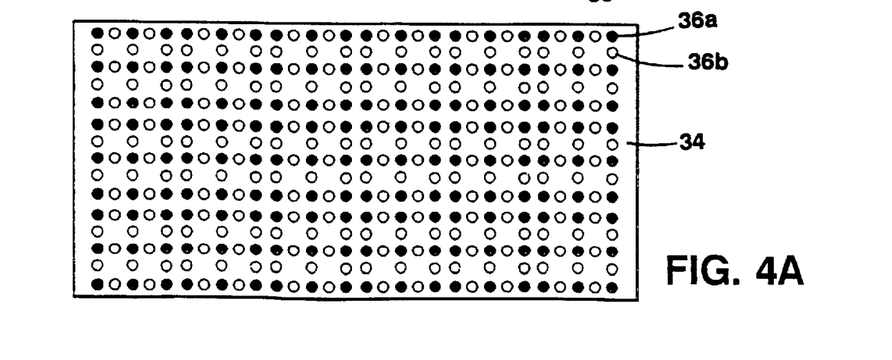

Referring now to the embodiment of FIGS. 4 and 4A, in this case a hairbrush presents an array of fibers in known position across the under surface of the hairbrush. Whereas individual fibers can be advantageously employed both as source fibers for delivering light to the tissue and at a later time as detector fibers while other fibers deliver light to the tissue, in some cases it is preferred to have special purpose fibers. That is the arrangement shown in FIGS. 4 and 4A. Light delivering or source fibers are indicated at 36a and detector fibers at 36b. Whereas a known location of the fibers is important, and a regular pattern is usually convenient, a regular pattern is not required. In fact to some extent there is a degree of irregularity in the pattern shown in FIG. 3A. The controller and processor for this array system can be employed in known ways. A common way is to illuminate a single fiber or single local group of fibers that act as a single fiber at any one time, and to proceed through the array on that basis, while taking readings from all of the detector fibers or groups of detector fibers that act as a single detection fiber. The resulting data in digital form is assembled as a matrix and suitably processed. By examination of the matrix after scanning through the entire array, it is possible to generate a back projection image of the area examined. Use of such a hairbrush with PM or TRS (pulse) techniques can enhance the image produced.

The freely extending end portions of the fibers of the hairbrush are constructed to extend through the depth of hair that is present for the particular application. Typically this depth may range in length from between 1 and 2.5 cm, dictating a freely extending fiber portion of similar or somewhat greater length. The particular stiffness of the freely extending fiber portions is determined based upon factors such as the sensitivity of the patient (e.g., a different stiffness being appropriate for adults than for young children), as well as taking into account the particular modulus of elasticity of the fiber material, (e.g., the modulus being different between glass and plastics), and the diameter and lengths of the fibers, and whether the fibers receive lateral support. These considerations determine the columnar properties of the individual fibers. Where the fibers are closely packed, and in particular, in the case of fine fibers, the degree of mutual support offered by neighboring fibers is taken into account in the selection of the parameters.

In general, the length/diameter ratio of the freely extending portions of the fibers from the hairbrush support or handle range between 5 and 200. A preferred range is between 20 and 150, and in a presently most preferred range, between about 50 and 125. The optical fibers have diameter of the order of 0.1 to 3 mm and in certain preferred conditions have a length between about 0.5 to 3 cm. In a particularly preferred region of selection, chosen for comfort, the fibers have a diameter of 0.2 to 0.5 mm and a length of about 1 to 2.5 cm.

In the simple instance of use of the imaging array of FIGS. 4 and 4A, using continuous wave spectrophotometric techniques, the fibers serving as source and the fibers serving as detection fibers are grouped to provide a four by four array resulting in 16 groupings of source and 16 groupings of detector fibers. Each group of source fibers is activated in turn for a period for example 16 seconds by the respective light source, which may be a conventional flashlight bulb. From this data, using analytical techniques described elsewhere, it is possible to define a back projection image that can be meaningful to determine presence of an occluding or unusual object such as a hematoma or breast tumor. Typically the controller and processor employed with this device have a memory and the hairbrush device itself is applied to a reference source. A suitable reference is a symmetrical portion on the other side of the body, and another, a previous reading at an earlier time from the identical location on the body now being examined. A difference between measurement and reference indicates an abnormality that suggests either therapy or more accurate, more expensive imaging procedures such as an MRI examination. Thus such devices as shown in FIGS. 3 and 4 can serve to screen when to use more expensive MRI imaging techniques.

Figure 5:
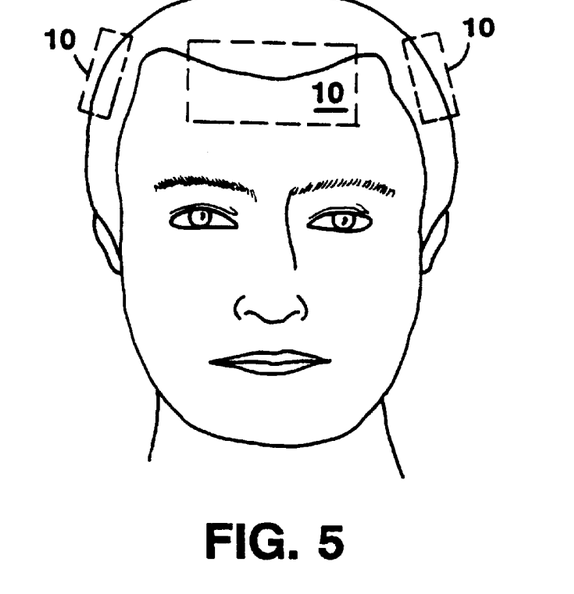
Figure 5A:
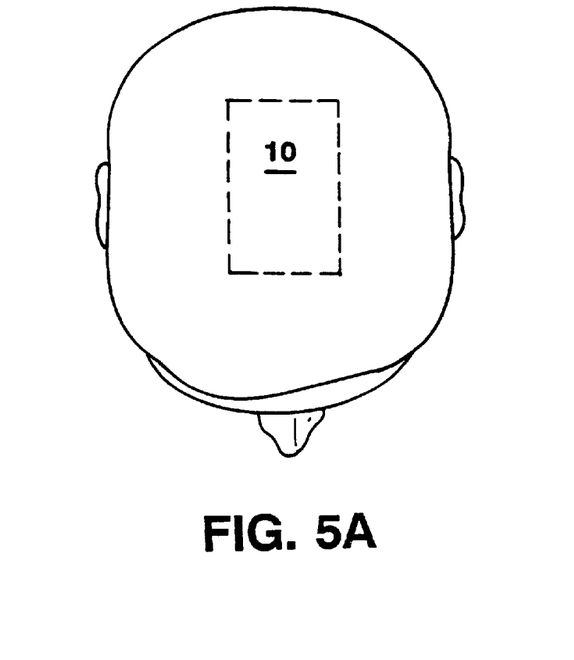
FIG. 5A illustrates use on the top of the head.

In FIG. 5, three locations for the hairbrush of FIG. 3 are shown. The hairbrush placed on the left side may be used to produce reference data for the hairbrush placed on the right side of the head and vice versa. On the other hand, the hairbrush may simply be moved over the object of interest to observe differences that may have been caused by abnormalities, e.g., to monitor recurrence of hematoma.

Figure 6:
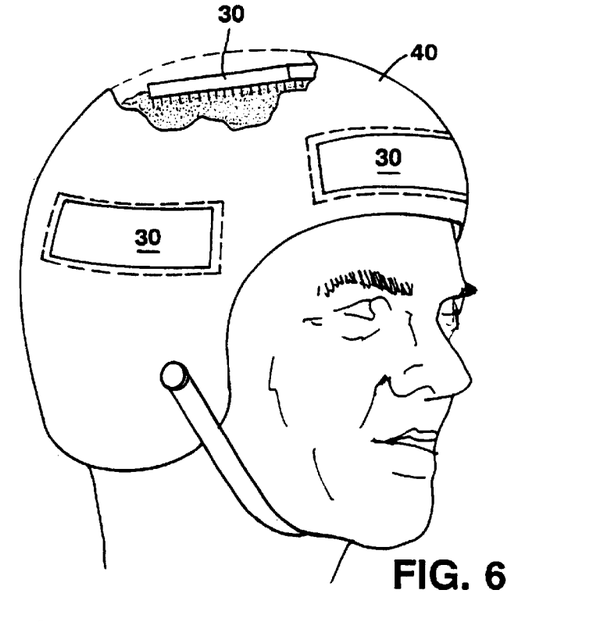
FIG. 6 illustrates a hat or helmet constructed to guide into position "hairbrush" optical coupling devices.

Referring to FIG. 6, in the case of use of hairbrushes as pictured in 4 and 4A, precise positioning is especially important to set a base line. The helmet has cutouts that are shaped as shown in 6B to receive the hairbrush 30, the cutout 44 being bounded by rigid sides 45 that serve as guides to precisely locate the hairbrush and guide it into engagement with the head, with the probes penetrating the free hair 42.

Figure 6A:
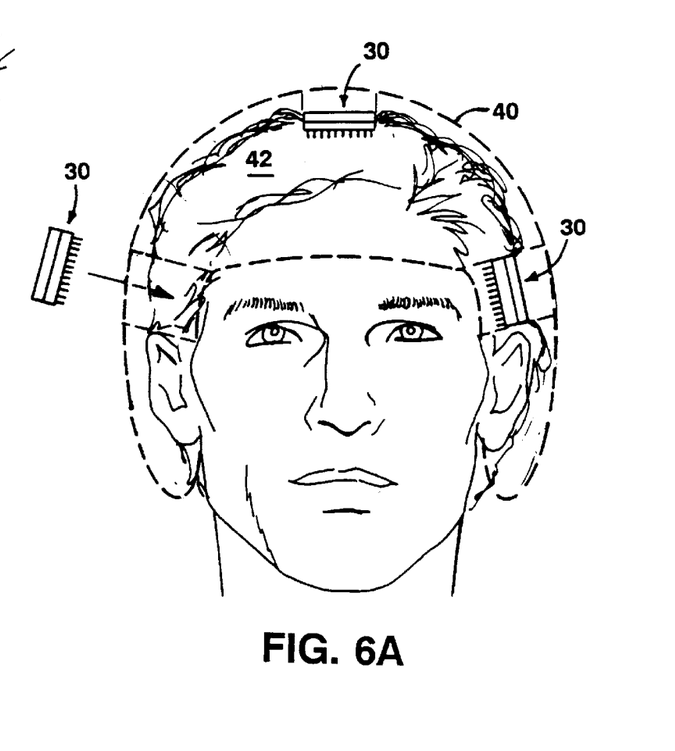
Figure 6B:
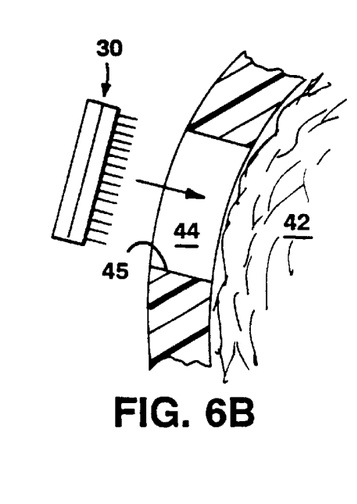
FIG. 6B is an enlarged cross-sectional view of a portion of the device of FIGS. 6 and 6A.

FIG. 6A shows guiding the hairbrush into the precisely known position on the sides and the top of the head.

FIG. 6 pictures diagrametrically a helmet or supporting structure with a chin strap that ensures the same position of the helmet from use to use. Not shown is a disposable, inflatable innerliner that adapts the helmet to different sizes and shapes of heads and locates the head in the helmet in a predetermined way. Such liners may be disposable after each use.

Figure 7:
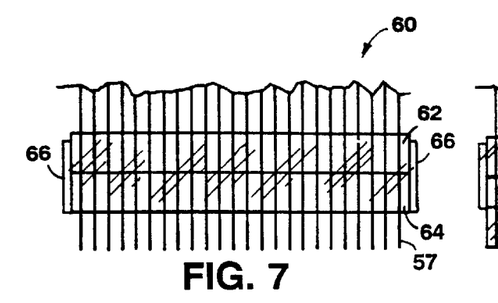
FIGS. 7–11 depict stages in the application of protective end tips on protruding fiber portions of a "hairbrush" optical coupler.

The set of FIGS. 7 through 11 are diagrammatic representations of a hairbrush optical coupler. The handle of the hairbrush 66 comprises an upper part 62 and a lower part 64. The upper part of the handle is fixed to the fibers at least during use, and the lower part of the handle is slidable along the fibers as it moves together or apart from the upper part of the handle. In FIG. 7 the parts are shown pushed together.

Freely extending fiber end portions 57 extend freely from the lower surface of the hairbrush, to penetrate the hair with the advantages that have been described. The fibers are shown to extend through the hairbrush at the top but in practice the fibers are gathered and taken by cable to the respective device such as the hematoma monitor, tumor detector or imager as described above. While the fibers are shown to be distributed uniformly, as would be the case with the imaging hairbrush shown in FIGS. 4 and 4A, they can be grouped in accordance with FIG. 3 or put in other arrangements as may be desired.

The purpose of FIGS. 7 through 11 is to illustrate in a general way the concept that protective covers may be applied to fibers and then removed and replaced from patient to patient. Likewise the hairbrush itself may be constructed to be sterilized as in a gas autoclave.

Referring to FIG. 7, as mentioned the ends of the fiber portions 57 extend below the hairbrush for a length suitable to penetrate the hair and reach the scalp. In the case the brush is used to achieve conformability and comfort against say the breast or a limb or the torso of the body, the length of the free end portions of the fibers is selected to perform that function.

Figure 8:
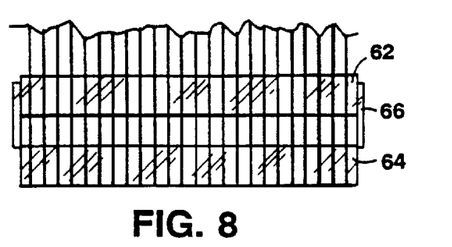

FIG. 8 is a first step in the sequence to apply protectors to the ends of the fibers. The lower portion 64 of the hairbrush handle is lowered to the ends of the fibers, sliding on guides 66 permanently mounted on the upper portion 62 of the hairbrush.

Figure 9:
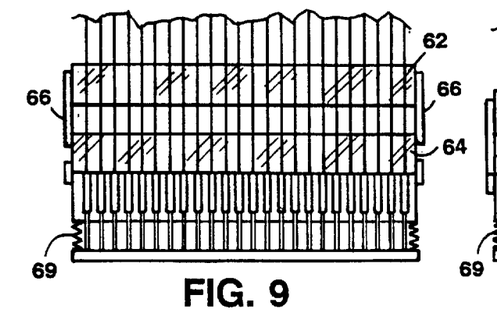
Figure 11:
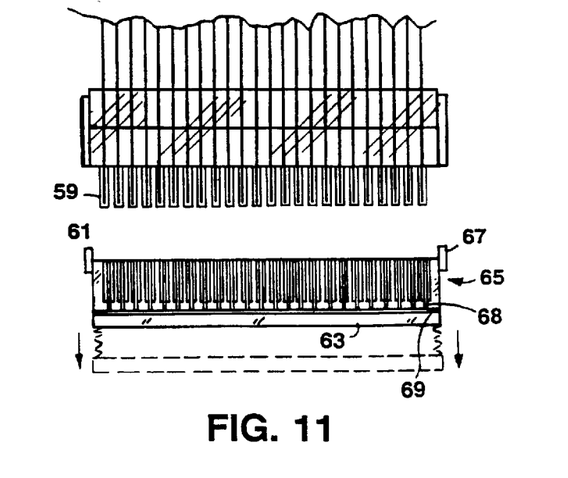
Figure 11A:
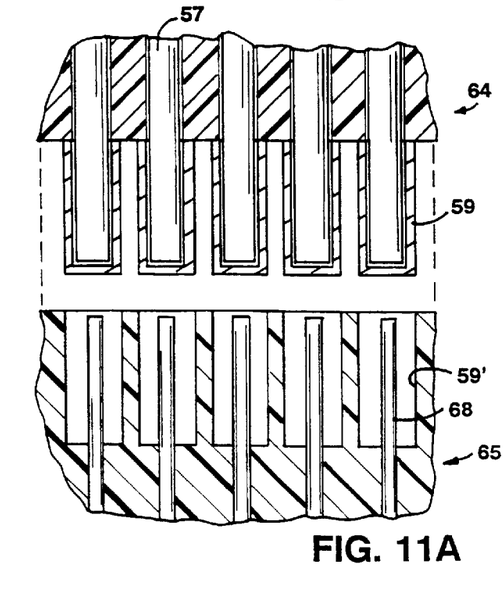

In the position of FIG. 8, the fiber ends are flush with the lower surface of the hairbrush handle. As illustrated in FIG. 9, a sleeve dispenser, also pictured at the lower part of FIG. 11, is then brought into registry with suitable guides on the hairbrush such that its dispensing surface is aligned with the lower surface of the hairbrush and protector-carrying cavities within the dispenser are precisely aligned with the fibers. This is made possible by guides 67 on the dispenser that engage appropriate grooves on the brush.

The dispenser 65 is comprised of a main body which, in the magnified views of FIGS. 9A through 11A, is seen to define cavities 59' in which protective sleeves 59 are placed. As shown in FIG. 9, the dispensing face of the dispenser is brought face to face with the lower surface of the handle portion 64. The fibers 57 align precisely with the hollow spaces of the sleeves 59, the fiber ends 57 being shown flush with the lower part of handle 64 in FIG. 9A.

Figure 9A:
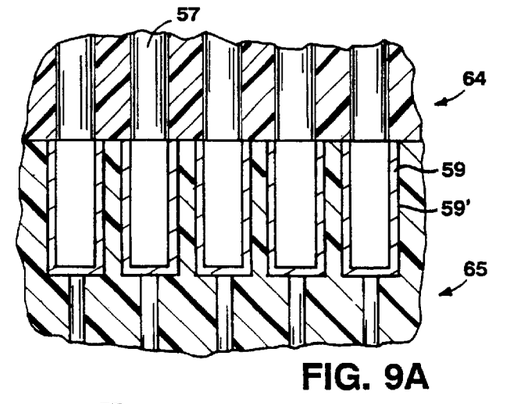
FIGS. 9A, 10A and 11A are magnified views of portions of the views of FIGS. 9, 10 and 11, respectively.

As shown also in FIG. 9A, the length of the sleeves is for instance of the order of five times the diameter of the fibers. The particular length depends upon how much length of the fibers is desired to be covered, which also may depend e.g., upon other means of cleaning or sterilization to be employed.

In important instances, not shown, the end sleeves extend the full length of the fibers and are integral with cover portions that cover the bottom of the hairbrush. The dispenser is effective in that case to apply the entire cover to the hairbrush.

Figure 10:
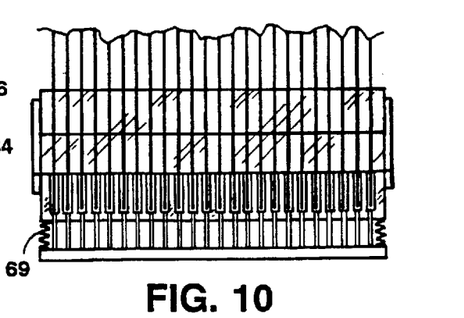
Figure 10A:
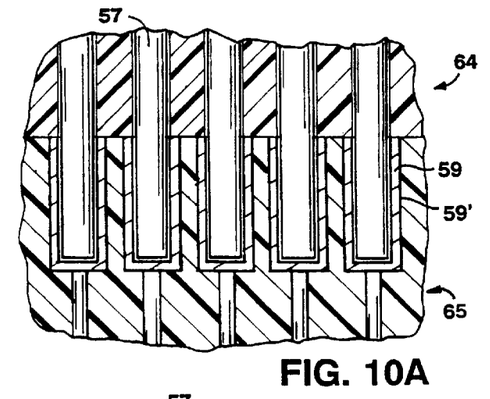

Returning to FIG. 9, in the position shown, the dispenser is engaged with the hairbrush while the hairbrush lower part is spaced away the from upper part. The position is determined by a stop provided by slide 66 protruding from the top portion of the hairbrush, that limits the travel of the lower portion to achieve a flush or slightly withdrawn condition. After the relationship of FIG. 9 is achieved, the upper portion of handle 62 is moved downwardly to engage the lower portion of the handle to the position shown in FIG. 11. Since the upper portion of the handle is fixed to the fibers, the fibers are thus carried forward, sliding in the lower portion of the handle, and the free ends of the fibers emerge from the lower part of the handle and enter the sleeves in the dispenser as depicted in FIG. 10. In case the fibers do not have sufficient columnar stiffness, tubular guides are employed between the upper and lower handle portions, one for each fiber, to prevent columnar collapse of the fibers and to ensure the sliding action just described.

At this point the end portions of the fibers have entered the protective sleeves. The lower portion of the dispenser comprises an activating bar 63 that is connected to a set of ejector pins, one associated with each of the sleeves within the dispenser. Compression springs 69 maintain the ejector bar in its lower position as shown in FIGS. 9 and 10. Upon depression of the ejector bar from the position of FIG. 10, the ejector pins engage the ends of the fibers and their sleeves and effectively push the protected end portions out of the dispenser to the position shown in FIG. 9. After this position is achieved, the ejector bar 63 collapsed against the lower portion of the dispenser, as shown in FIG. 11, is released with the springs 69 returning to the dotted line position shown in FIG. 11. The hairbrush as shown in FIG. 9 has freely extending fiber end portions housed in protective sleeves 59 and arranged to enter the head of hair or otherwise serve the functions that have been described.

In a preferred embodiment the sleeves are translucent teflon suitable to match with the substance of the skin to transfer light from source fibers to the head and detector fibers to transfer the light to the detector.

These sleeves are disposable and can be ejected. By moving the lower handle portion from the position in FIG. 9 to the position of FIG. 8, the lower part of the hairbrush handle strips the sleeves from the fibers which are discarded. Then, with the return of the handle position from the spaced apart position shown in FIG. 8, the condition of FIG. 7 is reachieved.

In certain instances it is unnecessary to have the fibers covered. In that case the device as shown in FIG. 7 can be used directly.

Figure 12:
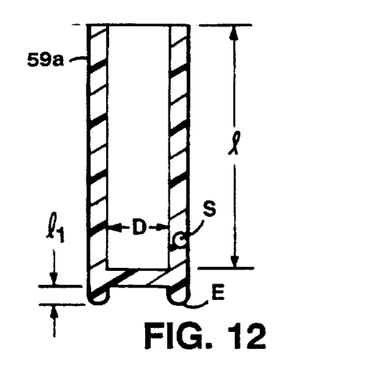
FIG. 12 is a side cross-sectional view on magnified scale of an end tip for fibers of a coupling device.
Figure 12A:
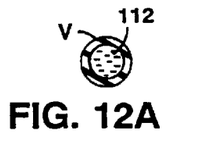
FIGS. 12A and 12B depict contrast members suitable for use in the end tip of FIG. 12.
Figure 12B:
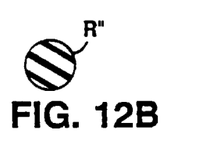
Figures 13, 14:
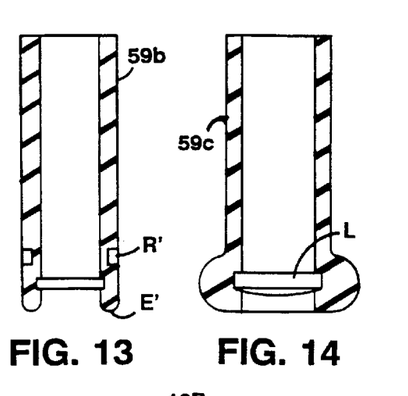
FIG. 13 is an alternative construction of an end tip having provision, for receiving a band-form contrast member.
FIG. 14 is a further embodiment of an end tip.

FIGS. 12, 13, and 14 illustrate alternate preferred forms of protective sleeves for the optical fibers. In FIG. 12 near the end of the fiber a socket S is provided in the substance of the protective cover 59a into which a suitably shaped contrast element can be inserted. Referring to FIG. 12A a contrast element vial V contains aqueous copper sulfate solution 112, which is a suitable contrast agent for MRI. The vial is of flexible material and can be deformed and inserted into the socket S shown in FIG. 12. In FIG. 12B sponge rubber ball R" is shown, suitable as a contrast agent for acoustic imaging. An insert of solid sodium iodide crystals is appropriate for xray. Different protective sleeves can be provided having different contrast agents, to enable dual mode examination, for instance with MRI or acoustic imaging. Other contrast agents for other modes of examination can be used.

Another feature of the embodiment of FIG. 12 is the annular end portion E of the sleeve which protrudes below the crossing plate that closes the bottom of the protective cavity formed by sleeve 59a. The optical fiber 57 is intended to extend the full length of that cavity and engage the bottom of the cavity, to be immersed in an optional optical matching fluid having the same refractive index as the fiber and the sleeve, to avoid a change of refractive index that can occasion light loss. The annular end portion E serves as a light dam or barrier. In the case that the material of the sleeve is uniformly translucent, an outer black coating or other means of achieving opacity is provided about the end tips. As the fiber is pressed against the tissue, the end tip E indents the fiber and creates an optical dam that prevents lateral movement of light and thus prevents false signal traveling along the engaged surface from reaching the detector. This arrangement prevents emission of such light when used on light source fibers: it also has utility for imaging fibers in the case of exposure to ambient light that may confound the measurement.

Figure 13A:
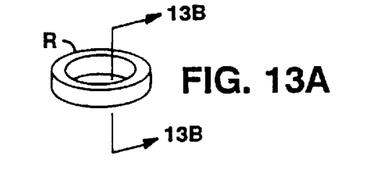
Figure 13B:
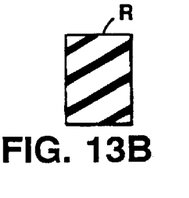
FIGS. 13B and 13C are cross-sections taken on line 13B of FIG. 13A illustrating cross-sections of two alternative contrast members for use with the end tip of FIG. 13.
Figure 13C:
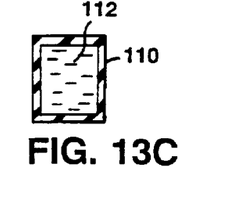

In the embodiment of FIG. 13 the substance of the tubular sleeve 59b is an opaque elastomer. The ends E' serve the function of the ends E in FIG. 12 and the cross member shown but not labeled in FIG. 13 serves to form the bottom cap and protect the fiber from contaminating conditions. The outer wall of the sleeve 59b is provided with a recess R' into which a contrast ring shown in FIG. 13A can be inserted. FIG. 13B illustrates a cross section of such a contrast ring, element R, of sponge rubber to serve as a contrast agent for acoustic imaging. In FIG. 13C the ring is hollow and has copper sulfate in aqueous solution contained by fluid impermeable walls 110 of the ring. Again, the ring can contain sodium iodide crystals. In FIG. 14 another preferred embodiment of the sleeve is shown in which instead of a plain plate forming the bottom of the elastomeric sleeve, a lens L is employed for the advantage of collecting additional light for transmission up the fiber. In the preferred embodiment of FIG. 14, the terminal end of the fiber is enlarged to provide sufficient area contact to provide comfort to the patient. The form is particularly useful with small or stiff fibers which have a tendency to produce pain. In other embodiments, instead of a separable element, the fibers themselves are configured to have enlarged end portions, for instance balls formed by melting the ends for achieving comfort. In such cases, the fibers are advantageously provided with an outer coating e.g. titanium dioxide paint or other pigment to achieve a diffusing condition to facilitate the transfer of light.

Figure 15:
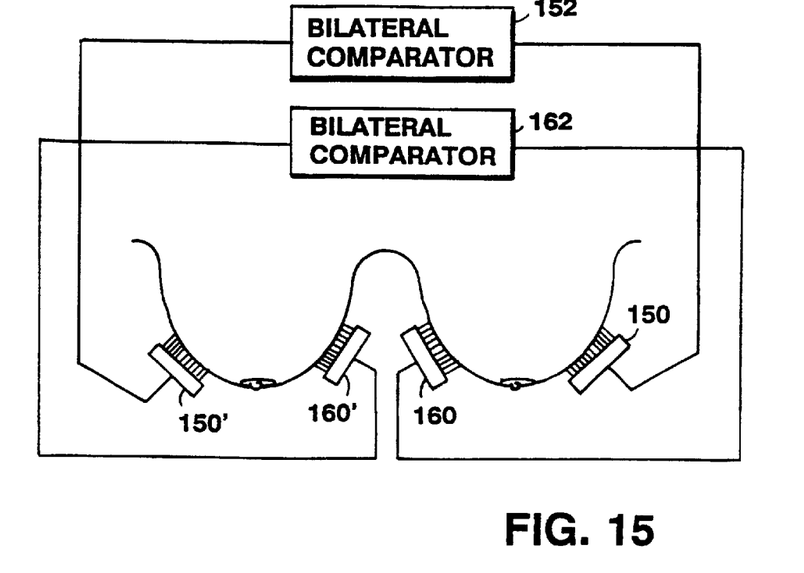
FIGS. 15 and 16 depict optical coupling systems constructed for examination of breast tissue.

Referring to FIG. 15, a breast examination system is shown employing brushes 150, 160 and 150' and 160'. The brushes are defined by a comfortable mass of free ended fibers that conform to the breast and transmit light in a desirable way. As shown the fibers extend across the entire base of the brush, however fibers arranged as in FIGS. 3 and 3a may also be employed. In each case, the signals from the relative symmetrical left and right inner breast surfaces are taken to bilateral comparator 162 whereas the similar signals from the outer surfaces of the left and right breasts, from detectors 150, 150', are taken to bilateral comparator 152. By further processing (not shown), the results of the two comparisons may be also correlated to further elaborate the examination.

Figure 16:
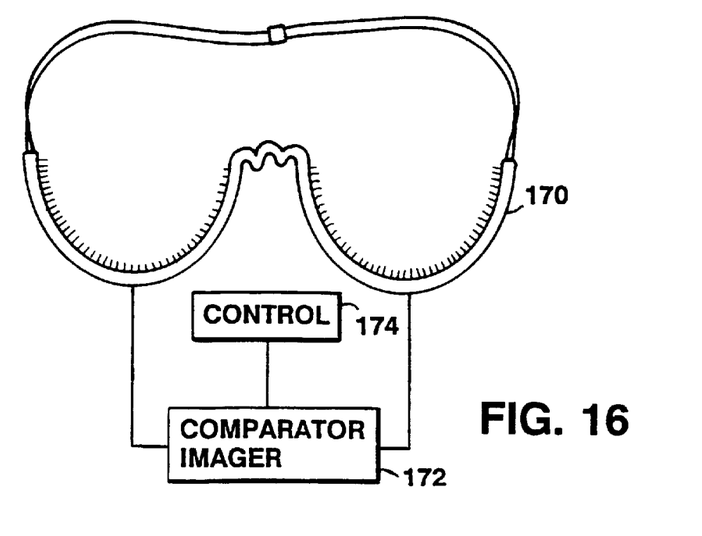

Referring to FIG. 16, a comfortable brassier like breast examination device is shown. In practice, it is possible to employ a transverse band of fibers, but in other instances the hemispherical surface of the brassier is entirely populated by the fibers in an array such as generally suggested in FIG. 4A. The brassier-like device is applied in the same way each time and enables the position from measurement to measurement to be accurately known so that comparison to a base-line condition can be made. Even without such reference, the examination is useful to determine presence of an inhomogene to identify a condition that requires further diagnosis. For daily monitoring, contrast agent is not suggested for use in this examination of breast tissue. In the event monitoring suggests a problem, a contrast agent may be administered to more effectively examine the tissue spectrophotometrically, or examination by another modality, though much more costly, may then be indicated.

In the case of the brassier or helmet it is advantageous to mold a suitable thermoplastic that softens at comfortable temperature, about the object to be examined, and when cooling, to use that form either directly as a guide to bring a hairbrush or other monitoring device into position for repetitive readings.

What is claimed is:
1. As part of an examination device, an input or output optical coupler device for transmitting photons between an optical source or detector and the brain or other suitable part of a body of a subject being examined, comprising:
    an array of optical fibers with end portions freely protruding as cantilevers from a support, said optical fibers being constructed and arranged for transmitting visible or near infra-red light,
    the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, said optical fibers being individually configured to provide separate optical coupling to a spectrophotometer.
2. The device of claim 1 further including diffusing means located at the fiber ends.
3. The device of claim 1 further including means for directing light into the fiber.
4. The device of claim 1 in which the fibers are single mode fibers.
5. The device of claim 1 in which the fibers are resiliently flexible laterally to bend and conform a pattern of fiber tips to variations in the shape of the skull, breast or other portion of the body.
6. The device of claim 1 in which the freely extending end portions of the fibers have a length to diameter ratio of between about 5 and 200.
7. The device of claim 6 in which the ratio is between about 20 and 150.
8. The device of claim 7 in which the ratio is between about 50 and 125.
9. The device of claim 1 in which the free end portions of the optical fibers have diameter of the order of 0.1 to 3.0 millimeter and have a length between about 0.5 to 3 cm.
10. The device of claim 9 in which the free end portions of the optical fibers have diameter of about 0.2 to 0.5 millimeter and length between about 1 and 2.5 cm.
11. The coupler device of claim 1, constructed as a handheld probe, and being sized and configured to be moved and placed against the front, sides and top of the head.
12. The coupler device of constructed as a handheld probe, and being sized and configured to be moved and placed against the breast.
13. The device of claim 1 wherein parts of the end portions of the fibers are enlarged to provide comfort to the subject.
14. The device of claim 1 wherein a lens is provided at the end of each optical fiber for gathering light that has passed through tissue.
15. The device of claim 14 wherein the fibers are single mode fiber.
16. The device of claim 1 wherein the ends of the fibers are comprised of a substance to diffuse light.
17. The device of claim 16 wherein the substance comprises titanium dioxide paint or coating applied to the end of the fiber.
18. As part of an examination device, an input or output optical coupler device for transmitting photons between an optical source or detector and the brain or other suitable part of a body of a subject being examined, comprising:
    an array of optical fibers with end portions freely protruding as cantilevers from a support, said optical fibers being constructed and arranged for transmitting visible or near infrared light, the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, and a second array of said optical fibers, wherein the first-mentioned array is associated with said source for transmitting light separately by individual fibers to the scalp or skin from the source, and the second array of fibers is associated with said detector for receiving light separately that has migrated to the scalp or skin from a known distance from the first-mentioned array of fibers for transmission to the detector.

19. The device of claims 1 or 18 in which the end portions of the fibers have smooth, enlarged tips adapted to comfortably engage the skin or scalp.

20. The optical coupler of claim 1 or 18 wherein said optical fibers are arranged with respect to said support to transmit selected pressure in a resiliently compliant manner.

21. As part of an examination device, an input or output optical coupler device for transmitting photons between an optical source or detector and the brain or other suitable part of a body of a subject being examined, comprising:

an array of optical fibers with end portions freely protruding as cantilevers from support, the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, and peripheral elements at the ends of at least some of the fibers arranged to engage the tissue to block transfer of light along the scalp or skin.

22. As part of an examination device, an input or output optical coupler device for transmitting photons between an optical source or detector and the brain or other suitable part of a body of a subject being examined, comprising:

an array of optical fibers with end portions freely protruding as cantilevers from a support, said optical fibers being constructed and arranged for transmitting visible or near infrared light, the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, wherein the fibers are disposed in a predetermined array, each fiber or small grouping of the fibers being associated with a discrete detector so that fiber tips simultaneously engage an area of the subject sufficient to provide data that enables processing to provide a back projection image.

23. The device of claim 22 arranged and connected to image the brain.

24. The device of claim 22 arranged and connected to image the breast.

25. As part of an examination device, an input or output optical coupler device for transmitting photons between an optical source or detector and the brain or other suitable part of a body of a subject being examined, comprising:

an array of optical fibers with end portions freely protruding as cantilevers from a support, said optical fibers being constructed and arranged for transmitting visible or near infrared light, the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, and the coupler device being arranged as a helmet or brassier, the fibers being adapted to simultaneously engage different sides of the portion of the subject being examined.

26. As part of an examination device, an optical coupler constructed and arranged as a conformable brush comprised of freely extending optical fiber end portions adapted to be positioned to engage the skin over an array of points on a body of a subject and to transmit or receive visible or near infra-red light that migrates through the tissue between input and receiving regions on the body for spectroscopic examination, said optical fibers providing optical coupling to a spectrophotometer.

27. The optical coupler of claim 26 sized and configured to be applied to the breast or breasts.

28. The optical coupler of claim 26 sized and configured to be applied to the arm or leg.

29. The optical coupler of claim 26 sized and configured to be applied to the testicle or testicles.

30. As part of an examination device, an optical coupler constructed and arranged as a conformable brush comprised of freely extending optical fiber end portions adapted to be positioned to engage the skin over an array of points on a body of a subject and to transmit or receive visible or near-infra-red light that migrates through the tissue between input and receiving regions on the body for spectroscopic examination, wherein said examination device is arranged as a hematoma detector, hematoma monitor, tumor detector, spectrophotometric imager or metabolic condition monitor.

31. A device comprising:

a disposable protective element adapted for engagement with the flesh of a subject comprising an end cup or sleeve disposably surrounding an end portion of an optical fiber freely protruding as a cantilever from a support, and further including several said optical fibers constructed to permit optical access between the ends of the fibers and the subject and to perform spectroscopic examination.

32. The device of claim 31, wherein said disposable protective element is used with a dispenser constructed to apply several said disposable elements to said free end portions of corresponding optical fibers.

33. The dispenser of claim 32 in which multiple end caps or sleeves are held in alignment by the dispenser in position to be entered by corresponding fibers by juxtaposition of said dispenser with a support from which the fibers can emerge.

34. A device comprising:

a disposable protective element adapted for engagement with the flesh of a subject comprising an end cup or sleeve disposably surrounding an end portion of an optical fiber freely protruding as a cantilever from a support, the support carrying several said optical fibers constructed to permit optical access between the ends of the fiber and the subject for spectroscopic examination, wherein an end region of the cup or sleeve carries a contrast medium.

35. The disposable element of claim 34 in which the contrast medium is adapted to provide contrast for examination by a modality other than light passing through the fibers.

36. The disposable element of claim 35 in which the contrast medium is selected to provide contrast for magnetic resonance imaging.

37. The disposable element of claim 35 in which the contrast medium is selected to provide contrast for acoustic imaging.

38. The disposable element of claim 34 in which the contrast medium is in a sphere, microsphere or other container.

39. The disposable element of claim 34 in which the contrast medium is a ring extending at least partially about the fiber.

40. As part of an examination device, an input or output optical coupler device for transmitting photons between an optical source or detector and the brain or other suitable part of a body of a subject being examined, comprising:

an array of optical fibers with end portions freely protruding as cantilevers from a support, the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, and a ferrule which extends beyond the end of the freely protruding fiber portion and is adapted to engage the tissue to prevent transfer of light along the surface of the engaged tissue.

41. The device of claim 40 wherein the ferrule is flexible and constructed to conform to the tissue.

42. The device of claim 40 wherein peripheral portions of the ferrule are comprised of light absorber.

43. As part of an examination device, an optical coupler constructed and arranged as a conformable brush comprised of freely extending optical fiber end portions adapted to be positioned to engage the skin over an array of points on a body of a subject for transmitting or receiving visible or near infra-red light that migrates through the tissue between input and receiving regions on the body for spectroscopic examination, further including another similar optical coupler, the couplers arranged to engage laterally symmetrical portions of the body, one to provide a reference for the other.

44. The optical coupler of claim 43 including a lateral comparator connected to both said optical couplers.

45. As part of an examination device, an input or output optical coupler device for transmitting photons between an optical source or detector and the brain or other suitable part of a body of a subject being examined, comprising:

an array of optical fibers with end portions freely protruding as cantilevers from a support, said optical fibers being constructed and arranged for transmitting visible or near infrared light, the end portions of the fibers fabricated, sized and distributed to penetrate freely extending hair when said support is placed on the head or other surface of the subject to make optical contact directly over an array of points with the surface of the scalp or skin below the free hair for transmitting or receiving light that migrates through the tissue between input and receiving regions on the head or other part of the body, wherein the optical coupler device is adapted to be connected to a plastic reference member molded to the contour of the subject.

46. A method of examination of subjects including:

providing an optical coupler, constructed to transmit photons between an optical source or a detector and biological tissue of the subject being examined, comprising an array of optical fibers with end portions freely protruding as cantilevers from a support in the manner of bristles from a hairbrush, the end portions of the fibers sized and distributed to penetrate freely extending hair on the surface of the subject to make optical contact directly over an array of points with the surface to transmit or receive light that migrates through the tissue between input and receiving regions, employing said coupler as an optical examination device using visible or near infrared light.

47. The method of claim 46 wherein said employing includes detecting hematoma in the biological tissue.

48. The method of claim 46 wherein said employing includes monitoring hematoma in the biological tissue.

49. The method of claim 46 wherein said employing includes detecting a tumor in the biological tissue.

* * * * *